United States Patent [19]

Sano et al.

[11] Patent Number: 4,606,826
[45] Date of Patent: Aug. 19, 1986

[54] APPARATUS FOR CONTROLLING ULTRAFILTRATION AND METHOD FOR THE SAME

[75] Inventors: Yoshihiko Sano, Suita; Mitsutaka Ueda, Otsu, both of Japan

[73] Assignee: Nissho Corporation, Osaka, Japan

[21] Appl. No.: 724,228

[22] Filed: Apr. 17, 1985

[30] Foreign Application Priority Data

Nov. 14, 1984 [JP] Japan .................................. 59-240312

[51] Int. Cl.$^4$ ............................................ B01D 13/00
[52] U.S. Cl. .................................... 210/646; 210/136; 210/321.3; 210/929
[58] Field of Search ............. 210/87, 929, 96.2, 321.3, 210/85, 136, 646, 86

[56] References Cited

U.S. PATENT DOCUMENTS

| | | | |
|---|---|---|---|
| 3,990,973 | 11/1976 | Boag et al. | 210/929 X |
| 4,021,341 | 5/1977 | Cosentino et al. | 210/929 X |
| 4,093,545 | 6/1978 | Cullis | 210/136 X |

*Primary Examiner*—Frank Spear
*Attorney, Agent, or Firm*—Armstrong, Nikaido, Marmelstein & Kubovcik

[57] ABSTRACT

An apparatus for controlling ultrafiltration in a dialysis system for artificial kidney including a dialyzer, a blood supply line for supplying a blood to the dialyzer, a blood discharge line for discharging the treated blood from the dialyzer, a liquid supply line for supplying a dialyzing liquid to the dialyzer, and a liquid discharge line for discharging the used dialyzing liquid from the dialyzer, and a negative pressure pump provided on the liquid discharge line, which comprises:

a bypass line for connecting said liquid supply line directly to said liquid discharge line and having a first control valve means;

a second control valve means disposed on said liquid discharge line in the upper stream of the junction of the liquid discharge line with the bypass line;

an ultrafiltration measuring line connected at its both ends to said liquid discharge line interposing said second valve means therebetween and equipped with a measuring chamber;

an air lead-in line having a third control valve means and a check valve means, with one end of said air lead-in line being connected to said ultrafiltration measuring line and the other end exposed to the atmosphere; and a liquid withdrawal control means comprising a pressure control circuit and a microcomputer, said control means electrically connecting to pressure gauges disposed at the blood inlet side and outlet side, respectively, of the dialyzer and pressure gauges disposed at the dialyzing liquid inlet side and outlet side.

8 Claims, 2 Drawing Figures

APPARATUS FOR CONTROLLING ULTRAFILTRATION AND METHOD FOR THE SAME

BACKGROUND OF THE INVENTION

The present invention relates to an apparatus for controlling ultrafiltration in a dialysis system for artificial kidney and a method for controlling ultrafiltration using the apparatus. More particularly, the present invention relates to an apparatus for controlling ultrafiltration adapted to perform an exact and automatic control of the amount of water withdrawn from the patient's blood in a dialyzer and a method for the control.

The method for determining an ultrafiltration rate (hereinafter referred to as UFR) which means the amount of liquid passed per unit of time through a semipermeable membrane from the blood side to the dialyzing liquid side in a dialyzer and controlling a transmembrane pressure (hereinafter referred to as TMP) which means a pressure difference between the blood side pressure of the membrane and the dialyzing liquid side pressure of the membrane, by means of an ultrafiltration controller, may be roughly classified into a positive pressure method and a negative pressure method.

The positive pressure method is such that the pressure difference between the blood side and the dialyzing liquid side, i.e. TMP, is controlled at a desired level by rendering the pressure on the blood side positive. Thus, a blood pump, for example, a roller pump, is provided on the arterial side of the blood circuit to drive the arterial blood. For example, a system based on this principle is described in Japanese Patent Unexamined Published Application (Kokai Tokkyo Koho) No. 59-95053.

The negative pressure method is such that the desired TMP is established by rendering the pressure on the dialyzing liquid side negative. Thus, a negative pressure pump is provided on a discharge line for discharging the used dialyzing liquid from the dialyzer. Apparatuses embodying this latter principle are described in Japanese Patent Unexamined Published Application Nos. 57-66761, 56-84606 and 55-49117, for instance.

While the ultrafiltration controller according to the present invention belongs to the category of negative pressure type, this category of apparatuses may take such constructions as the one employing a flow meter as a means for measuring the amount of ultrafiltrate (see Japanese Patent Unexamined Published Application No. 55-49117), the one employing a volumetric device such as a measuring cup or a metering pump and computing the average value of UFR (see Japanese Patent Unexamined Published Application Nos. 56-84606 and 57-175218), and the one in which a controller designed such that the amount of dialyzing liquid fed to the dialyzer is equalized with the amount of filtrate to be discharged from the dialyzer is used and the amount of ultrafiltrate is computed as a difference between the amount of the filtrate emerging from the dialyzer and the amount of the dialyzing liquid fed to the dialyzer (see Japanese Patent Unexamined Published Application No. 57-66761). Herein, the term "filtrate" is intended to mean the dialyzing liquid discharged from the dialyzer which contains the ultrafiltrate.

As to the method of determining TMP, in view of the difficulty in measuring directly the average pressure on the blood side as well as on the dialyzing liquid side, the TMP computation formula: $TMP = P_B - P_D + \Delta P$, wherein $P_B$ is a pressure on blood side and $P_D$ is a pressure on dialyzing liquid side, with a correction factor $\Delta P$ has been proposed to permit a computation of a more exact TMP value (see Japanese Patent Unexamined Published Application No. 59-75057).

However, the conventional ultrafiltration control system of the positive pressure type is disadvantageous in that an exact pressure control cannot be accomplished since the blood level in a blood chamber fluctuates when controlling the blood side pressure.

In the conventional system of the negative pressure type wherein a flow meter is used as a means of measuring UFR, an expensive flow meter or flow chamber must be employed and, in addition, the accuracy of determination tends to drop since metabolic wastes and other foreign matter deposit on these devices. In the system wherein a measuring cup is employed as a means of measuring the amount of ultrafiltrate, the cup can be emptied only by feeding air with a roller pump or the like, so that there are problems not only in the aspect of maintenance but also in terms of cost. Moreover, when UFR is to be measured at a low TMP value and the patient's venous blood pressure is high, the dialyzing liquid side pressure must be rendered positive to ensure the low TMP value in some cases, but when the filtrate is discharged from the measuring cup by exposing the circuit to the atmosphere and the dialyzing liquid side pressure is made positive, the remaining filtrate may flow back into the measuring cup due to compression of air in the ultrafiltration measuring line. Moreover, the filtrate may enter into the measuring cup due to vibrations, etc. prior to measuring.

The system wherein a metering pump is used for measurement of UFR has the disadvantage that in prolonged use the tubing undergoes plastic deformation which results in decrease in the accuracy of determination. Further, the system provided with a means of determining the amount of ultrafiltrate as a difference between the amount of filtrate and the amount of dialyzing liquid fed has the disadvantage that, because many solenoid valves are required, deposits of metabolic wastes and other foreign matter to the valves lead to a decrease in accuracy and sufficient deaeration must be provided so as to prevent attachment of tiny air bubbles.

In regard to the method of controlling ultrafiltration, too, the difference in $\Delta P$ between the case in which a dialyzing liquid is flowing through the dialyzer and the case in which the dialyzing liquid is not flowing and the fact that the value of $\Delta P$ varies with different patients have not been fully taken into consideration and because of the consequent inaccuracy of $\Delta P$, substantial errors have been inevitable.

It is a primary object of the present invention to resolve the above-mentioned problems and provide an inexpensive ultrafiltration controller device capable of providing an exact and automatic control of the amount of liquid withdrawn from the patient's blood.

Another object of the invention is to provide an ultrafiltration controlling method capable of providing an accurate and automatic control of the amount of liquid withdrawn from the patient's blood.

These and other objects of the present invention will become apparent from the description hereinafter.

SUMMARY OF THE INVENTION

The present invention provides an apparatus for controlling ultrafiltration in a dialysis system for artificial kidney including a dialyzer, a blood supply line for supplying a blood to the dialyzer, a blood discharge line for discharging the treated blood from the dialyzer, a liquid supply line for supplying a dialyzing liquid to the dialyzer, a liquid discharge line for discharging the used dialyzing liquid from the dialyzer, and a negative pressure pump provided on the liquid discharge line, which comprises;

a bypass line for connecting said liquid supply line directly to said discharge line and having a first control valve means;

a second control valve means disposed on said liquid discharge line in the upper stream of the junction of the liquid discharge line with the bypass line;

an ultrafiltration measuring line connected at its both ends to said liquid discharge line interposing said second valve means therebetween and equipped with a measuring chamber;

an air lead-in line having a third control valve means and a check valve means, with one end of said air lead-in line being connected to said ultrafiltration measuring line and the other end exposed to the atmosphere; and a liquid withdrawal control means comprising a pressure control circuit and a microcomputer, said control means electrically connecting to pressure gauges disposed at the blood inlet side and outlet side, respectively, of the dialyzer and pressure gauges disposed at the dialyzing liquid inlet side and outlet side, respectively, of the dialyzer, and level sensors adapted to detect liquid level in said measuring chamber and said negative pressure pump.

DETAILED DESCRIPTION

Figure 1:
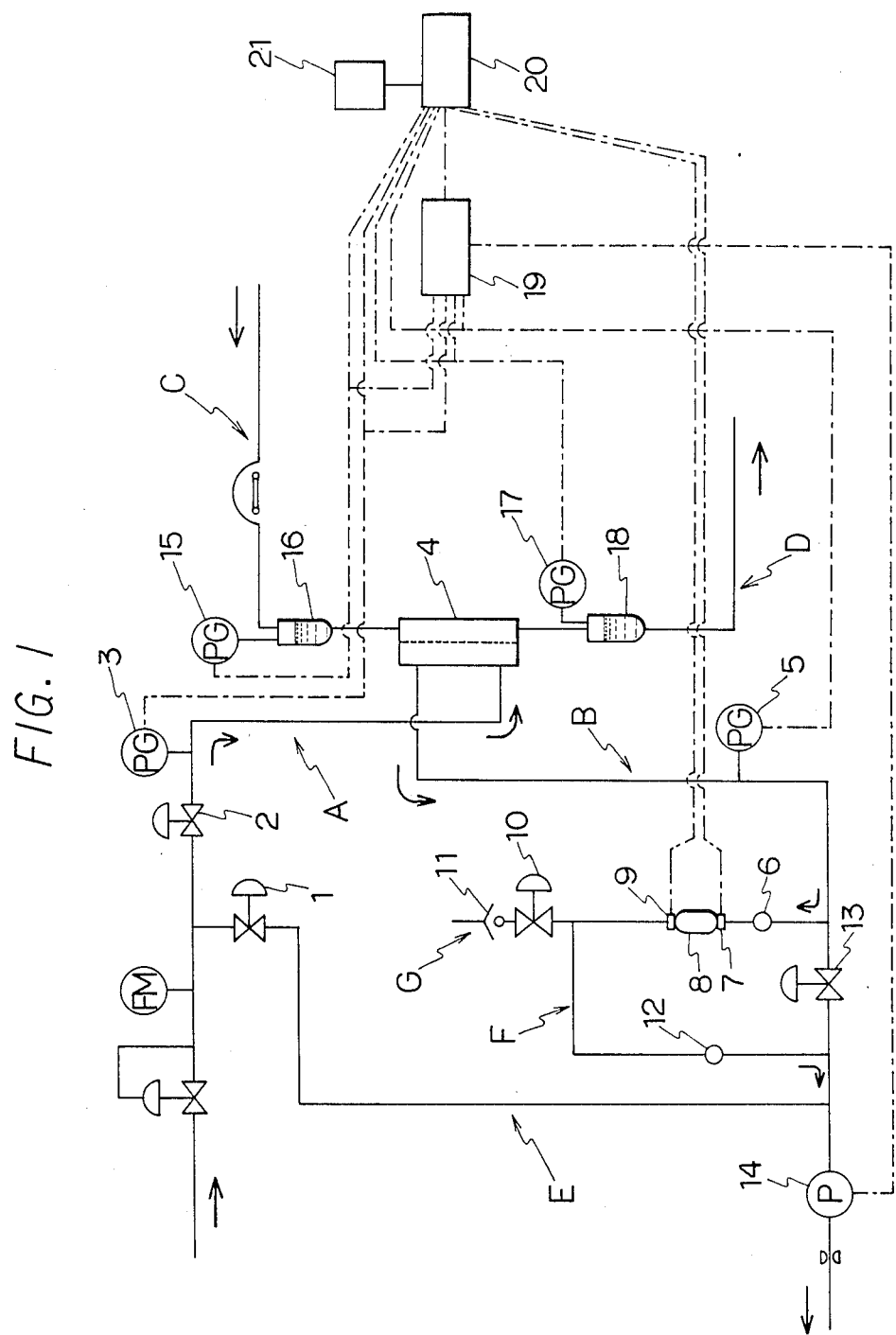
FIG. 1 is a schematic diagram illustrating an artificial kidney dialysis system including the ultrafiltration controller according to the present invention.

The present invention includes the following embodiments:

(1) The above-mentioned liquid withdrawal controller includes a means for computing UFR on the basis of the amount of ultrafiltrate determined in the ultrafiltration measuring line, computing TMP from blood side pressure and dialyzing liquid side pressure and determining an ultrafiltration performance (hereinafter referred to as UFRP) from the TMP value and the UFR value, a means for computing TMP corresponding to a predetermined UFR value with use of the above UFRP value and controlling the suction pressure of the negative pressure pump to provide a dialyzing liquid side pressure corresponding to the thus computed TMP value.

(2) Since the present invention employs a measuring chamber for determining the amount of ultrafiltrate, the problems inherent in this type of system are solved by providing:

(1) as a means of discharging the filtrate from the measuring chamber, an air lead-in line disposed overhead of the measuring chamber;

(2) as a means of preventing a backflow of the filtrate into the measuring chamber, a liquid basin disposed at the outlet side of the measuring chamber; and (3) as a means of preventing entry of the filtrate into the measuring chamber prior to measuring due to the influence of vibrations and the like, an additional liquid basin disposed at the inlet side of the measuring chamber.

(3) Moreover, for an exact control of ultrafiltration, a method for minimizing the error of ΔP in the formula for computation of TMP has been developed.

(a) In the case that, on the dialyzing liquid side, the pressure at the dialyzing liquid inlet side of the dialyzer (hereinafter referred to as $P_{Din}$) and the pressure at the dialyzing liquid outlet side of the dialyzer (hereinafter referred to as $P_{Dout}$) are to be measured, the TMP computation formula:

$$TMP = \frac{P_A + P_V}{2} - \frac{P_{Din} + P_{Dout}}{2} + \Delta P_1 \quad (I)$$

wherein $P_A$ is the arterial side pressure immediately before the blood inlet of the dialyzer, $P_V$ is the venous side pressure immediately after the blood outlet of the dialyzer, and $\Delta P_1$ is a correction factor, is used, irrespective of whether a dialyzing liquid is flowing or not in the dialyzer.

(b) In the case that either $P_{Din}$ or $P_{Dout}$ only is to be measured on the dialyzing liquid side, (b-1) in the case that a dialyzing liquid is flowing through the dialyzer, the TMP compution formula:

$$TMP = \frac{P_A + P_V}{2} - P_D + \Delta P_2 \quad (II)$$

wherein $P_D$ is the measured $P_{Din}$ or $P_{Dout}$ and $\Delta P_2$ is a correction factor, or (b-2) in the case that a dialyzing liquid is not flowing through the dialyzer, the TMP computation formula:

$$TMP = \frac{P_A + P_V}{2} - P_D + \Delta P_2' \quad (III)$$

wherein $\Delta P_2'$ is a correction factor, is used.

One of the above TMP computation formulae (I), (II) and (III) is used in conjuction with the formula: TMP=UFR/UFRP, and two optional UFR values determined by varying the suction pressure of the negative pressure pump and the values of $[(P_A+P_V)/2-(P_{Din}+P_{Dout})/2]$ (when either $P_{Din}$ or $P_{Dout}$ only is to be determined, the values of $[(P_A+P_V)/2-P_D]$) corresponding to the above UFR values are substituted into the above formulae to obtain ΔP (in this case, $\Delta P_1$, $\Delta P_2$ and $\Delta P_2'$). Since ΔP substantially does not change throughout dialysis treatment, it can be determined before initiation of dialysis.

The ultrafiltration controller of the present invention has the following advantages.

(1) In view of the difference in the correction factor ΔP for TMP between the case in which a dialyzing liquid is flowing through the dialyzer and the case in which the liquid is not flowing, there is provided a liquid withdrawal control means improved in this aspect. This liquid withdrawal control means is adapted to determine a more exact value of TMP and control the suction pressure of the negative pressure pump to provide a dialyzing liquid side pressure corresponding to this TMP value, with the result that it affords the measurement of a more exact amount of water withdrawn from the patient.

(2) In the downstream of the measuring chamber in the ultrafiltration measuring line, there is provided an air lead-in line. This air lead-in line is designed to expose the ultrafiltration measuring line to the atmosphere so that the filtrate is readily discharged from the measuring chamber and is advantageous over the conventional roller pump device in both maintenance and cost.

(3) The liquid basin disposed at the inlet side of the measuring chamber in the ultrafiltration measuring line is designed to detain the filtrate that may flow towards the measuring chamber due to vibrations or the like prior to commencement of measuring and serves to prevent entry of the filtrate into the measuring chamber before measuring the amount of ultrafiltrate.

(4) The liquid basin disposed at the outlet side of the measuring chamber in the ultrafiltration measuring line is adapted to detain the filtrate that may backflow when the dialyzing liquid side pressure is rendered positive after the measuring chamber is emptied and serves to prevent entry of the filtrate into the measuring chamber before measuring the amount of ultrafiltrate.

The preferred embodiment of the present invention will be described by referring to the accompanying drawings.

As shown in FIG. 1, an apparatus for controlling ultrafiltration according to the present invention is a main component of a dialysis system for an artificial kidney consisting of a dialyzer 4, a liquid supply line A for supplying a dialyzing liquid to the dialyzer 4, a liquid discharge line B for discharging used dialyzing liquid from the dialyzer and equipped with a negative pressure pump 14, a blood supply line C for supplying the blood from a patient's artery to the dialyzer, and a blood discharge line D for discharging the treated blood from the dialyzer and returning back it to the patient's vein.

The ultrafiltration controller of the present invention comprises a bypass line E for a temporary interruption of flow of the dialyzing liquid to be fed to the dialyzer 4, a control valve 13 disposed in the upper stream of the junction of the liquid discharge line B and the bypass line E, an ultrafiltration measuring line F connected at both ends thereof to the liquid discharge line B with the control valve 13 interposed therebetween, an air lead-in line G, one end of which communicates with the ultrafiltration measuring line F with the other end exposed to the atmosphere, and a liquid withdrawal controller which has a means for controlling the amount of liquid withdrawn from the patient's blood through a semipermeable membrane in the dialyzer 4 and a means for integration and display of the cumulative amount of liquid withdrawal during dialysis treatment. The control valve 13 may be a directional control valve operated by any drive means including electromagnetic drive, electromotor drive or hydraulic drive. A solenoid operated valve is preferably used. As the control valves mentioned below, such valve can be also used.

The above-mentioned bypass line E is provided with a control valve 1 adapted to remain closed during dialysis treatment and open only when the supply of dialyzing liquid to the dialyzer 4 is temporarily interrupted.

The ultrafiltration measuring line F is adapted to measure the amount of ultrafiltrate while the bypass line E is open, i.e. during the above-mentioned temporary interruption of supply of the dialyzing liquid to the dialyzer 4, and comprises a measuring chamber 8 which is bulged in its central portion and constricted at its both ends, level sensors 7, 9 disposed in the constrictions at both ends of the measuring chamber 8, and liquid basins 6, 12 disposed in the upper stream and dawnstream of the measuring chamber 8 for preventing the filtrate from entering the chamber before measuring the amount of ultrafiltrate. Usually, the ultrafiltration measuring line F stands up substantially vertically from the liquid discharge line B. The liquid basins 6, 12 may be any optional devices only if they serve to prevent the filtrate from entering the measuring chamber 8 prior to measuring and as long as they are made of transparent or translucent material, each may be either a spherical vessel or a cylindrical vessel or a tube of large diameter.

The air lead-in line G is adapted to withdraw the filtrate from the measuring chamber by exposing the ultrafiltration measuring line F to the atmosphere and comprises a control valve 10 and a check valve 11 adapted to prevent liquid leakage. The location of the check valve 11 may be either forwardly or backwardly of the control valve 10. As to the point of connection of the air lead-in line G, it may be anywhere on the ultrafiltration measuring line F but in consideration of the factor of gravity, it is preferably located directly overhead of the measuring chamber 8.

With regard to the liquid withdrawal controller, it comprises a pressure control circuit 19 and a microcomputer 20, and these two components are electrically interconnected to each other. Also, they are electrically connected to pressure gauges 3, 5, 15, 17 disposed on the dialyzing liquid side and blood side of the dialyzer 4, and level sensors 7, 9 and a negative pressure pump 14 (as shown by broken lines in FIG. 1). The liquid withdrawal controller includes a means for computing UFR from the amount of ultrafiltrate measured by the measuring chamber 8, computing TMP from the blood side pressure and dialyzing liquid side pressure, and determining UFRP (=UFR/TMP) from this TMP value and the UFR value, and a means for computing a TMP value corresponding to a predetermined UFR value from the above UFRP value and controlling the negative pressure pump 14 to provide a dialyzing liquid side pressure corresponding to this TMP value.

The operation for control of the ultrafiltration rate will be described below. A dialyzing liquid is fed through the liquid supply line A to the dialyzer during dialysis treatment, and after dialysis and ultrafiltration of the patient's blood, the used dialyzing liquid flows through the liquid discharge line B and the ultrafiltration measuring line F and is withdrawn from the system by the suction force of the negative pressure pump 14. On the other hand, the blood from the patient's artery flows through a blood supply line C and an arterial pressure chamber 16 to the dialyzer 4 where it is dialyzed and ultrafiltered. The treated blood is returned back through a venous pressure chamber 18 to the patient's vein.

To measure the amount of ultrafiltrate, a control valve 2 such as a solenoid operated valve on the liquid supply line A is closed and the control valve 1 on the bypass line E is opened to temporarily interrupt the flow of dialyzing fluid to the dialyzer 4. Since, in this condition, the dialyzer 4 is supplied only with the blood, the amount of ultrafiltrate can be determined by measuring the amount of filtrate after stop of dialyzing liquid supply.

To measure the amount of ultrafiltrate, the supply of dialyzing liquid to the dialyzer 4 is stopped in the first place and the control valve 10 on the air lead-in line G and the control valve 13 on the liquid discharge line B are opened to withdraw the filtrate from the ultrafiltration measuring line F. After the filtrate has been completely discharged, the above-mentioned two control valves 10, 13 are closed, whereupon the filtrate solely derived from the blood in the absence of a dialyzing liquid, i.e. the filtrate resulting from ultrafiltration flows out from the dialyzer 4 into the ultrafiltration measuring line F via the liquid discharge line B. Therefore, the amount of ultrafiltrate can be determined by measuring the volume of the above filtrate.

Referring, now, to the liquid withdrawal controller, in measuring the amount of ultrafiltrate, the time at which the ultrafiltrate begins to flow into the measuring chamber 8 and the time when the measuring chamber 8 becomes full of the ultrafiltrate are detected by level sensors 7 and 9, respectively, and sent as electric signals to a microcomputer 20. In this microcomputer 20, UFR is computed from the time difference between the times detected by the above two level sensors 7, 9 and the capacity of the measuring chamber 8.

Then, when the control valve 1 on the bypass line E is closed and the control valve 2 on the liquid supply line A is opened, the dialyzing liquid is again fed to the dialyzer 4. At this moment, pressure data, $P_{Din}$ and $P_{Dout}$ from a pressure gauge 3 and a pressure gauge 5 disposed at the dialyzing liquid inlet side and outlet side, respectively, of the dialyzer 4, and $P_A$ and $P_V$ from a pressure gauge 15 and a pressure gauge 17 disposed at the blood inlet side and outlet side, respectively, of the dialyzer 4 are supplied as electric signals to the microcomputer 20, where TMP is computed from the above-mentioned UFR using TMP computation formula: $TMP=(P_A+P_V)/2-(P_{Din}+P_{Dout})/2+\Delta P_1$ and, further, UFRP (=UFR/TMP) is computed from this TMP value and the above UFR value.

Then, when the UFR value set for a particular patient is inputted into the microcomputer 20, the microcomputer 20 computes TMP corresponding to the set UFR using the previously computed UFRP mentioned above and directes the pressure control circuit 19 to control the suction pressure of the negative pressure pump 14 so as to provide a dialyzing liquid side pressure corresponding to the above TMP value. Moreover, in the microcomputer 20, the cumulative total amount of the water withdrawn from the patient's blood (=dialysis period of time ×TMP×UFRP) is computed and displayed on a display panel 21. Since, in dialysis treatment, the UFRP of the dialyzer 4 decreases gradually with time in the course of dialysis, the UFRP is repeatedly corrected, for instance, 30 minutes, 1 hour, 2 hours and so forth after initiation of dialysis so that TMP may be brought into correspondence with the set UFR value.

The ultrafiltration controller according to the present invention is designed so that the pressure on the dialyzing liquid side can be measured at both the inlet side and outlet side. This is to account for the pressure loss due to the viscous drag of the dialyzing liquid flowing through the dialyzer 4 and permits a more accurate determination of TMP as compared with the determination at either the inlet side or the outlet side. Actually, however, the pressure loss due to the viscous drag of the dialyzing liquid is considerably smaller than the pressure loss due to the viscous drag of the blood. For example, the pressure loss at a dialyzing liquid flow rate of 500 ml/min. is generally 10 to 20 mmHg, while the pressure loss on the blood side is generally 30 to 80 mmHg at a blood flow rate of 200 ml/min. and a hematocrit value of 25%. Thus, since the viscous drag is proportional to the flow rate and dialysis treatment is generally carried out at a dialyzing liquid flow rate of 500 ml/min. or less, a fairly accurate TMP value can be obtained by measuring either the inlet or the outlet pressure only as far as the dialyzing liquid side is concerned. In this case, TMP can be computed using the TMP computation formula: $TMP=(P_A+P_V)/2-P_D+\Delta P_2$ (or $\Delta P_2'$).

Figure 2:
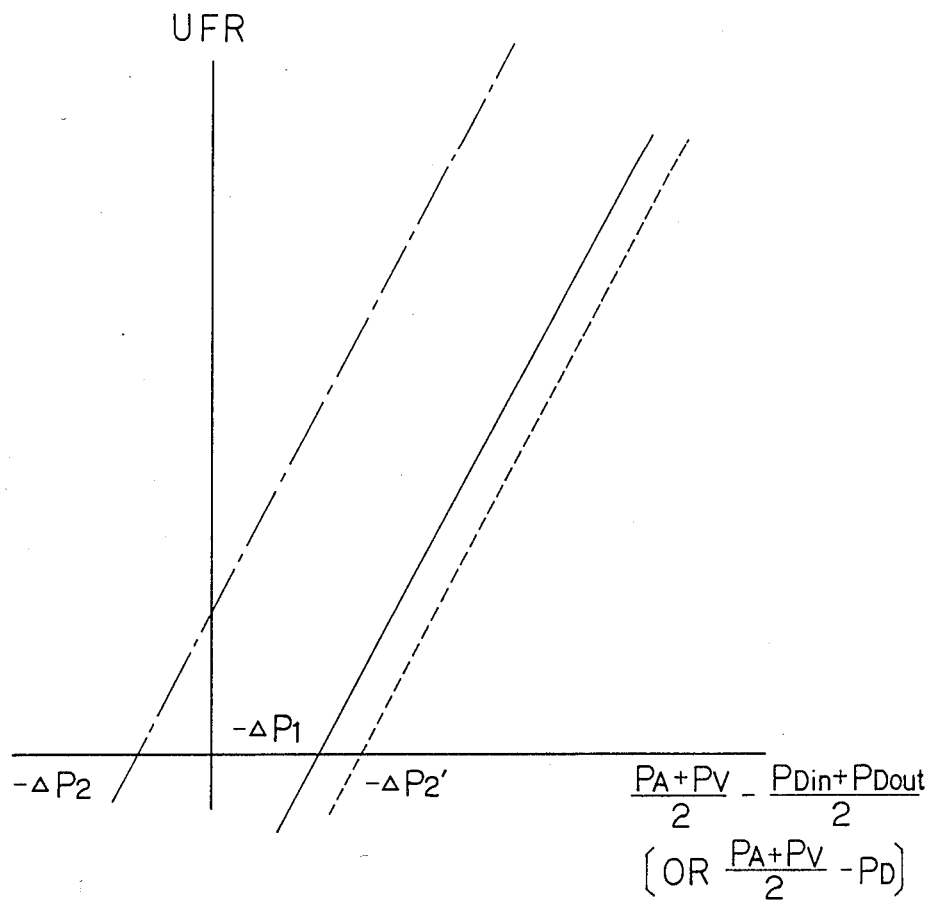
FIG. 2 is a graph showing the relation between UFR and $[(P_A+P_V)/2-(P_{Din}+P_{Dout})/2]$ or $[(P_A+P_V)/2-P_D]$.

Now, $\Delta P_1$ (or $\Delta P_2$, $\Delta P_2'$) can be determined prior to initiation of dialysis as follows. Since the relation between UFR and $(P_A+P_V)/2-(P_{Din}+P_{Dout})/2$ [or $(P_A+P_V)/2-P_D$] can be expressed as a linear function with UFRP as gradient as shown in FIG. 2, one may select two optional values for UFR and then compute $\Delta P_1$ using the UFR values, the values of $[(P_A+P_V)/2-(P_{Din}+P_{Dout})/2]$ (or the values of $[(P_A+P_V)/2-P_D]$), and TMP computation formulae: $TMP=(P_A+P_V)/2-(P_{Din}+P_{Dout})/2+\Delta P_1$ (or $TMP=(P_A+P_V)/2-P_D+\Delta P_2$) and $TMP=UFR/UFRP$.

As has been explained hereinbefore, the ultrafiltration controller according to the present invention has the following advantages:

(1) Since none of the expensive precision flow meter, flow chamber, and other devices are required, the determination inaccuracy due to deposits of metabolic wastes, etc. is no longer encountered. Instead, a less expensive ultrafiltration controller with a comparatively high accuracy can now be provided.

(2) Since the viscous drag of dialyzing liquid is taken into account, a more accurate control on the amount of water withdrawn can be ensured.

(3) Since the amount of water withdrawn can be controlled as desired, TMP can be adjusted according to the time-course change of UFRP during dialysis treatment so as to maintain the amount of water withdrawn at a constant level.

(4) Since a check valve is disposed on the air lead-in line, fouling of the floor due to liquid leakage does not take place any longer.

(5) Since the air lead-in line is used in instead of a roller pump, the construction is more advantageous in terms of maintenance and cost.

The present invention has been particularly described and explained by means of the preferred embodiments. These embodiments are intended to illustrate the invention and not be construed to limit the scope of the invention. It is to be understood that various changes and modifications may be made in the invention without departing from the spirit and scope thereof.

In addition to the parts or elements used in the embodiments, other parts or elements can be used in the embodiments as set forth in the specification to obtain substantially the same results.

What we claim is:

1. An apparatus for controlling ultrafiltration in a dialysis system for artificial kidney including a dialyzer, a blood supply line for supplying a blood to the dialyzer, a blood discharge line for discharging the treated blood from the dialyzer, a liquid supply line for supplying a dialyzing liquid to the dialyzer, and a liquid discharge line for discharging the used dialyzing liquid from the dialyzer, and a negative pressure pump provided on the liquid discharge line, which comprises:

a bypass line for connecting said liquid supply line directly to said liquid discharge line and having a first control valve means;

a second control valve means disposed on said liquid discharge line in the upper stream of the junction of the liquid discharge line with the bypass line;

an ultafiltration measuring line connected at its both ends to said liquid discharge line interposing said second valve means therebetween and equipped with a measuring chamber;

an air lead-in line having a third control valve means and a check valve means, with one end of said air lead-in line being connected to said ultrafiltration measuring line and the other end exposed to the atmosphere; and a liquid withdrawal control means comprising a pressure control circuit and a microcomputer, said control means electrically connecting to pressure gauges disposed at the blood inlet side and outlet side, respectively, of the dialyzer and pressure gauges disposed at the dialyzing liquid inlet side and outlet side, respectively, of the dialyzer, and level sensors adapted to detect liquid level in said measuring chamber and said negative pressure pump.

2. The apparatus of claim 1, wherein said ultrafiltration measuring line comprises, in association with said measuring chamber, level sensors disposed at the inlet end and the outlet end, respectively, of the measuring chamber, and liquid basins disposed at the inlet side and the outlet side, respectively, of the measuring chamber.

3. The apparatus of claim 1, wherein said air lead-in line is disposed overhead of said measuring chamber.

4. The apparatus of claim 1, wherein said liquid withdrawal control means comprises a means for computing an ultrafilatration rate (UFR) on the basis of the amount of ultrafiltrate determined in said ultrafiltration measuring line, computing a transmembrane pressure (TMP) from blood side pressure and dialyzing liquid side pressure and determining an ultrafiltration performance (UFRP) from said TMP and UFR, a means of computing TMP corresponding to a predetermined UFR value with use of said UFRP and controlling the suction pressure of said negative pressure pump to provide a dialyzing liquid side pressure corresponding to said TMP value, and a means of computing and displaying a cumulative amount of water withdrawn during dialysis treatment.

5. A method for controlling ultrafiltration in a dialysis system for artificial kidney which comprises: in association with an apparatus for controlling ultrafiltration in a dialysis system for artificial kidney including a dialyzer, a blood supply line for supplying a blood to the dialyzer, a blood discharge line for discharging the treated blood from the dialyzer, a liquid supply line for supplying a dialyzing liquid to the dialyzer, and a liquid discharge line for discharging the used dialyzing liquid from the dialyzer, and a negative pressure pump provided on the liquid discharge line, which comprises:

a bypass line for connecting said liquid supply line directly to said liquid discharge line and having a first control valve means;

a second control valve means disposed on said liquid discharge line in the upper stream of the junction of the liquid discharge line with the bypass line;

an ultafiltration measuring line connected at its both ends to said liquid discharge line interposing said second valve means therebetween and equipped with a measuring chamber;

an air lead-in line having a third control valve means and a check valve means, with one end of said air lead-in line being connected to said ultrafiltration measuring line and the other end exposed to the atmosphere; and a liquid withdrawal control means comprising a pressure control circuit and a microcomputer, said control means electrically connecting to pressure gauges disposed at the blood inlet side and outlet side, respectively, of the dialyzer and pressure gauges disposed at the dialyzing liquid inlet side and outlet side, respectively, of the dialyzer, and level sensors adapted to detect liquid level in said measuring chamber and said negative pressure pump;

computing UFR on the basis of the amount of ultrafiltrate determined in said ultrafiltration measuring line;

computing TMP using one of the following TMP computation formulae:

(a) in the case that, on the dialyzing liquid side, the pressure at the dialyzing liquid inlet side of the dialyzer ($P_{Din}$) and the pressure at the dialyzing liquid outlet side of the dialyzer ($P_{Dout}$) are to be measured, $$TMP = \frac{P_A + P_V}{2} - \frac{P_{Din} + P_{Dout}}{2} + \Delta P_1 \qquad (I)$$

wherein $P_A$ is the arterial side pressure immediately before the blood inlet of the dialyzer, $P_V$ is the venous side pressure immediately after the blood outlet of the dialyzer, and $\Delta P_1$ is a zeroing correction factor for TMP as determined prior to the initiation of dialysis treatment, irrespective of whether a dialyzing liquid is flowing or not through the dialyzer, (b) in the case that either $P_{Din}$ or $P_{Dout}$ only is to be measured on the dialyzing liquid side, (b-1) in the case that a dialyzing liquid is flowing through the dialyzer, $$TMP = \frac{P_A + P_V}{2} - P_D + \Delta P_2 \qquad (II)$$

wherein $P_D$ is the measured $P_{Din}$ or $P_{Dout}$ and $\Delta P_2$ is a correction factor for TMP, or (b-2) in the case that a dialyzing liquid is not flowing through the dialyzer, $$TMP = \frac{P_A + P_V}{2} - P_D + \Delta P_2' \qquad (III)$$

wherein $\Delta P_2'$ is a correction factor for TMP, computing UFRP from said TMP value and said UFR value, computing a TMP value corresponding to a predetermined UFR value using said UFRP value, and controlling said negative pressure pump to provide a dialyzing liquid pressure corresponding to the last-mentioned TMP value.

6. The method of claim 5, wherein $\Delta P_1$ in the TMP computation formula (I) is obtained by selecting two optional UFR values obtained by varying the suction pressure of the negative pressure pump, and computing $\Delta P_1$ by using said two UFR values, two values of $$\frac{P_A + P_V}{2} - \frac{P_{Din} + P_{Dout}}{2}$$

corresponding to said two UFR values, and the following two formulae:

$$TMP = \frac{P_A + P_V}{2} - \frac{P_{Din} + P_{Dout}}{2} + \Delta P_1, \text{ and}$$

$$TMP = UFR/UFRP.$$

7. The method of claim 5, wherein $\Delta P_2$ in the TMP computation formula (II) is obtained by selecting two optional UFR values obtained by varying the suction pressure of the negative pressure pump under the condition that the dialyzing liquid is flowing through the dialyzer, and computing $\Delta P_2$ by using said two UFR values, two values of $$\frac{P_A + P_V}{2} - P_D$$

corresponding to said two UFR values, and the following two formulae:

$$TMP = \frac{P_A + P_V}{2} - P_D + \Delta P_2, \text{ and}$$

$$TMP = UFR/UFRP.$$

8. The method of claim 5, wherein $\Delta P_2'$ in the TMP computation formula (III) is obtained by selecting two optional UFR values obtained by varying the suction pressure of the negative pressure pump under the condition that the dialyzing liquid is not flowing through the dialyzer, and computing $\Delta P_2'$ by using said two UFR values, two values of $$\frac{P_A + P_V}{2} - P_D$$

corresponding to said two UFR values, and the following two formulae:

$$TMP = \frac{P_A + P_V}{2} - P_D + \Delta P_2', \text{ and}$$

$$TMP = UFR/UFRP.$$

* * * * *